United States Patent [19]
Vincent et al.

[11] Patent Number: 4,855,909
[45] Date of Patent: Aug. 8, 1989

[54] FORENSIC SAMPLE TRACKING SYSTEM AND PRINT STATION THEREFOR

[75] Inventors: Kent D. Vincent; Carl A. Myerholtz, both of Cupertino, Calif.

[73] Assignee: Hewlett-Packard Company, Palo Alto, Calif.

[21] Appl. No.: 123,489

[22] Filed: Nov. 20, 1987

[51] Int. Cl.$^4$ .................. G06F 15/42; G01D 9/00
[52] U.S. Cl. .................. 364/413.01; 364/413.07; 235/375; 422/64; 346/33 ME; 101/38.1
[58] Field of Search .................. 235/375, 385, 462; 364/413.01, 413.02, 413.07; 422/63, 64, 65, 66, 67; 154/384, DIG. 47; 101/35, 36, 37, 38 R; 400/103, 104; 346/33 ME

[56] References Cited

U.S. PATENT DOCUMENTS

| | | | |
|---|---|---|---|
| 3,526,125 | 9/1970 | Gilford et al. | 422/65 |
| 3,656,473 | 4/1972 | Sodickson et al. | 346/33 ME |
| 3,778,790 | 12/1973 | Proust et al. | 346/33 ME |
| 4,164,320 | 8/1979 | Irazoqui et al. | 235/375 |
| 4,595,562 | 6/1986 | Liston et al. | 422/65 |

Primary Examiner—A. D. Pellinen
Assistant Examiner—H. L. Williams
Attorney, Agent, or Firm—Robert P. Sabath; Edward Y. Wong

[57] ABSTRACT

A forensic sample and tracking system includes a computer system which operates a data base and a read/write station. The assignment of an identifier in the data base and an identification code to be printed on a sample bottle label are coordinated by the computer. An identification code can then be read for verification after it is written. This permits automated verifying of identification codes in a heretofore unavailable manner. The read/write station makes use of an inexpensive, reliable and compact thermal ink jet print head so that a field computer and read/write station can be taken to sample collection sites. The effective linear resolution of the identification code is enhanced using a two-track bar code.

15 Claims, 3 Drawing Sheets

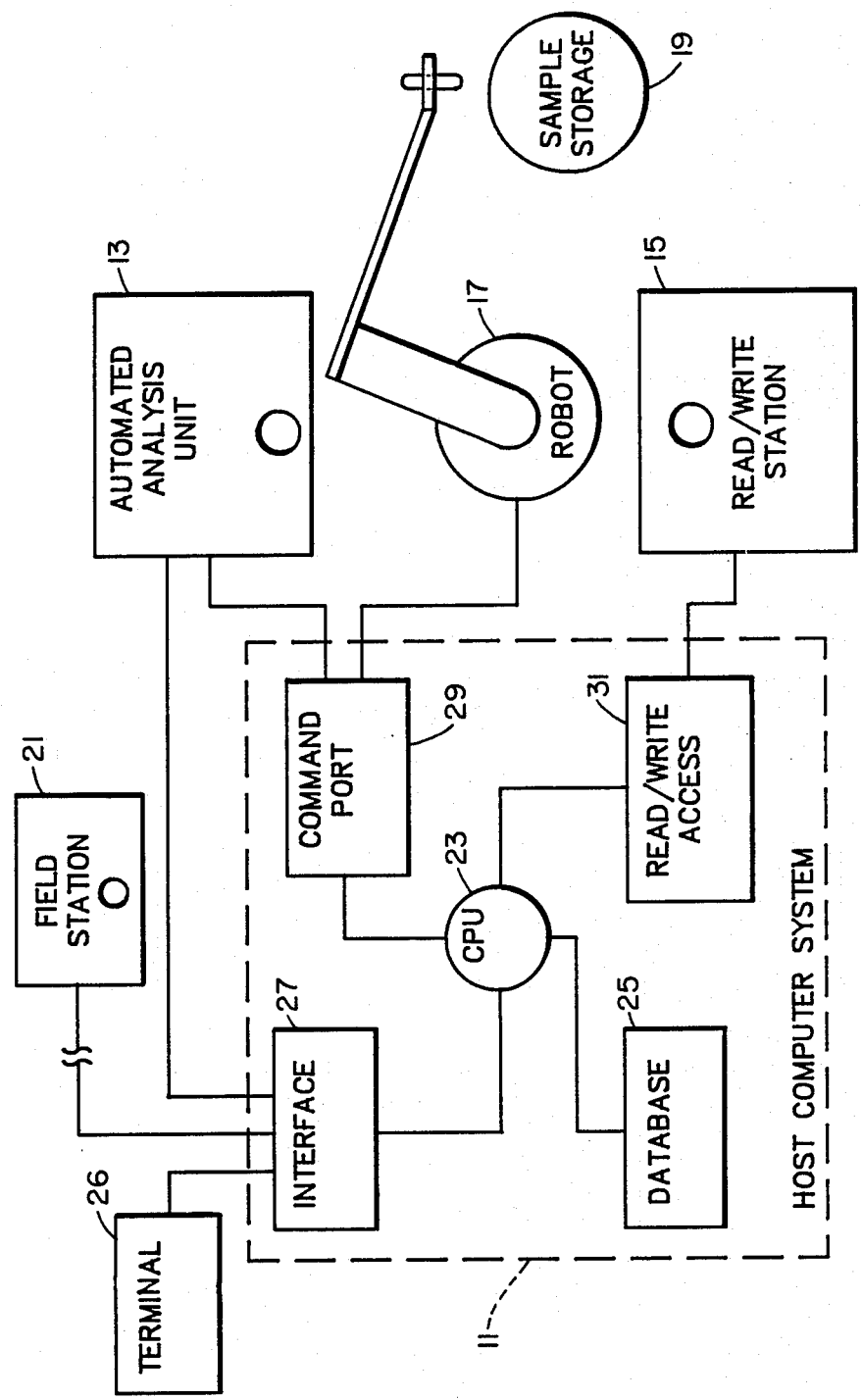
FIG._1.

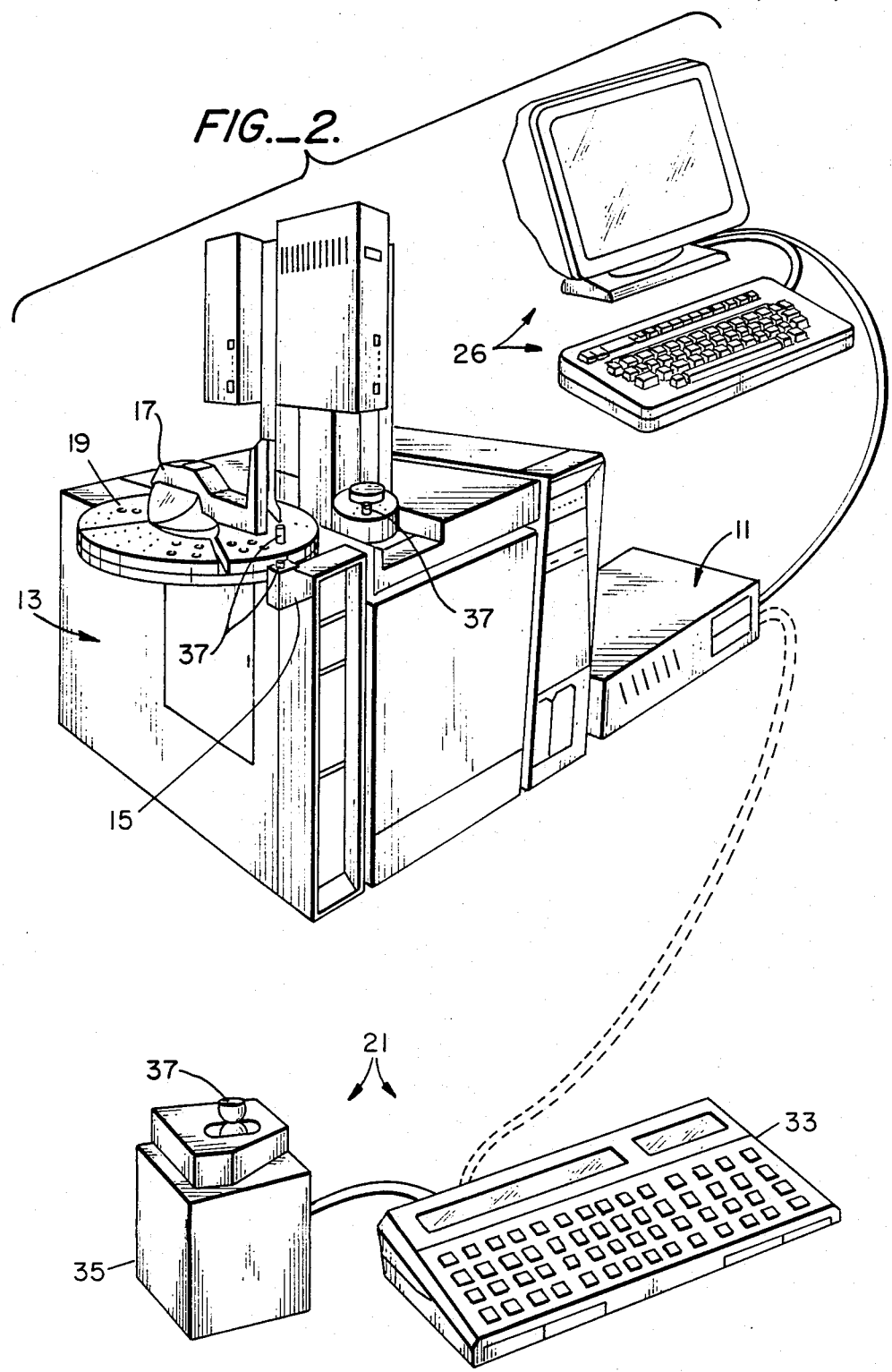
FIG._2.

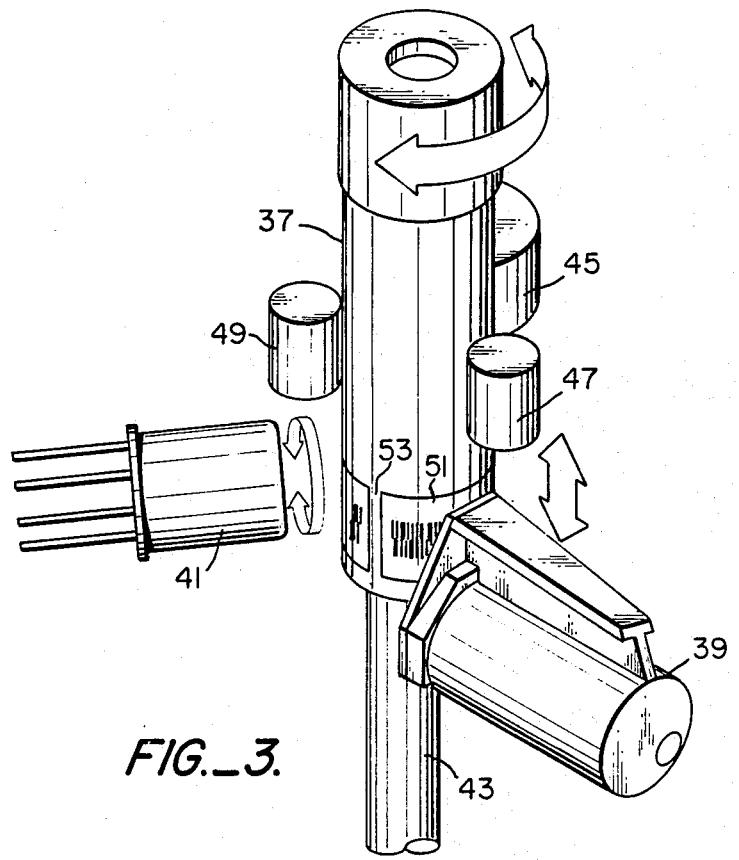
FIG._3.
FIG._4.

FORENSIC SAMPLE TRACKING SYSTEM AND PRINT STATION THEREFOR

BACKGROUND OF THE INVENTION

The present invention relates to sample tracking systems and, more particularly, to a sample tracking system to provide for writing sample data on a sample container.

A major objective of the present invention is to provide for flexible and reliable sample tracking for forensic chemical analysis labs. In forensic analysis it is necessary that the sample to which a description refers be identifiable, even years after analysis is completed.

A prevalent concern of such laboratories is the considerable amount of paperwork required to track a sample through various stages of collection, distribution, preparation and chemical analysis. It is commonly understood that in a given study, there is about a 60% to 70% chance of clerical error, and a significant proportion of these result in misidentification of a sample. In court, this could translate into strong evidence against the wrong suspect. More generally, this error rate largely undermines the validity and, thus, usefulness of chemical analysis in establishing the guilt of a polluter or drug user "beyond a reasonable doubt".

In a typical laboratory procedure there are plenty of opportunities for error. Collection can involve, for example, filling a bottle with river water downstream of a suspected polluter. Inevitably, this bottle will be stored among many similar bottles. It is therefore important that the bottle be uniquely identified so that information such as the time, date and place of collection be determinable at all times in the ensuring analytical and forensic chain of events. Ideally, the time, date and place are indicated on the sample bottle. The data may be handwritten on a label, either before or after application to the container. Opportunity for error exists in application of a label prepared off the bottle or, at a later stage, reading the handwriting in the bottle. A portable printer can be used to overcome legibility problems, but then there is a greater chance of a typographical or other input error.

Once the sample is brought into the laboratory, it is usually transferred to several bottles. The information must be transferred to the new bottles as well as to the laboratory data base, providing further opportunities for reading and data entry errors. Similar errors can occur at sample preparation and analysis. Various levels of redundancy can be built into a procedure, but usually add complexity, and thus additional opportunities for error.

The opportunity for mistakes in data entry and reading can be largely eliminated by using bottles with pre-printed serialized bar code labels at each step of the laboratory procedure. However, preprinted bar code labels do not lend themselves to time, date and location data, thus not meeting legal requirements for some studies. Furthermore, while pre-printed labels can include text as well as bar code, it is difficult to conceive of a system for providing mnemonically encoded data on a pre-printed label. The lack of mnemonic codes increases the chances of human error during manual analytic, inventory and forensic procedures.

What is needed is a sample tracking system providing for flexible and reliable sample tracking. Such a system should minimize opportunities for read and write errors, both in the field and in the laboratory. In addition, the system should permit considerable flexibility in assigning mnemonically encoded data to be displayed on a container label. Further, the system should be simple to use, without requiring redundant operator procedures.

SUMMARY OF THE INVENTION

The present invention provides a sample tracking system including a computer interfaced to a write station, which can also incorporate a read function. The write station can also include a print head and a read sensor. The write station can be made compatible with commonly used cylindrical glass sample bottles by incorporating means for rotating a bottle relative to the print head and the read sensor during write and read operations.

A complete sample tracking system can include both a host system and a portable system. The portable system can include a portable computer with a companion read/write station. The host system can also include automated distribution, preparation and analysis equipment.

The print head can be a thermal ink jet print head, similar to that used in the Thinkjet Printer manufactured by Hewlett Packard Company as Product Number HP82225B. Unlike most other printer types in which mechanical components impact, or at least contact a print surface, only fluid contacts the print surface when a thermal ink jet is used. Thus, thermal ink jet printers are unlikely to break a sample bottle or disturb sample contents. In addition, the selected print head is compact, reliable and inexpensive, and ideally suited for write stations, especially where portability is a factor.

Since such print heads cannot match lithography for linear resolution, a modified bar code format using parallel tracks of bar code can be implemented. This is made practical by the read/write station's ability to meet much more stringent mechanical read tolerances than a manually operated bar code wand. The read function can be used to locate the beginning and end of a blank label so that the printing can be appropriately positioned on the label.

The system of the present invention provides for reliable sample tracking. The assignment of identification codes to be printed on bottles can be substantially automated, with negligible room for human error and ample automated verification procedures, both in the field and in the laboratory. Computer assisted assignment of identification codes provides considerable flexibility in assigning mnemonic codes while providing a ready check against duplicate assignments. In addition, the system is convenient to use and vastly reduces the paper work that has plagued analytical laboratories. Further features and advantages of the present invention are apparent in the description below with reference to the following drawings.

BRIEF DESCRIPTION OF THE DRAWINGS

FIG. 1 is a schematic view of an integrated sample treatment and tracking system incorporating read/write stations in accordance with the present invention.

FIG. 2 is a perspective view of the system of FIG. 1.

FIG. 3 is a schematic perspective view of a read/write station of FIG. 1.

FIG. 4 is a plan view of a label with parallel track bar code as printed by the read/write station of FIG. 3.

DESCRIPTION OF THE PREFERRED EMBODIMENTS

An automated sample analysis and tracking system comprises a computer system 11, an automated analysis unit 13, a read/write station 15, a robot 17, a sample storage rack 19, and a field station 21, as shown in FIGS. 1 and 2. Host computer system 11 includes a central processing unit or CPU 23 which manages a data base 25. Communication between CPU 23 and an operator terminal 26 and between CPU 23 and field station 21 is via a computer interface 27. Automated analysis unit 13 and the robot 17 are controlled via a command port 29, while the results of analysis are fed back to hose computer system 11 through interface 27. Read/write station 15 is controlled via a read/write access port 31.

Data base 25 is the central repository of information about samples, containing information about each sample collected and processed by the sample treatment and tracking system. The data base information corresponding to each sample is assigned a unique, and preferably, mnemonic, identifier.

Read/write station 31 serves to read and write identification codes on bottles containing samples or analytic derivatives thereof. An identification code can be the identifier used by the data base, perhaps with additional information, such as the date of sample collection. More generally, the identification code can assume any form printable by the write station, provided the identification code is somehoe referable to the corresponding identifier so that a description in the data base is associated with the right sample.

To ensure a correspondence of samples and descriptions, the writing of the identification code is directed by CPU 23 which also controls data base 25. This arrangement ensures that identification data sent to read/write station 31 conforms to the data base identifier. By reading the code after it is written, the identification code can be verified against the identifier in data base 25. This minimizes errors assigning identification codes and considerably enhances the reliability of sample tracking.

Automated analysis unit 13 includes, for example, a chromatograph. Preferably, analysis unit 13 is a combination of sample distribution and preparation modules and several analytical tools, and can be spatially distributed rather than monolithic. Robot 17 is an arm which transports sample bottles from sample storage rack 19 to read/write station 15 and to analysis unit 13 as commanded by the CPU 23.

Field station 21 is a combination of a portable computer 33 and a bottle printer 35, as shown in FIG. 2. Mechanically, bottle printer 35 is similar to read/write station 15. Portable computer 33 includes on board data base capability sufficient for sample collection or other purposes not requiring access to the host computer data base 25. Host computer system 11 and the field station 21 communicate through interface 27 so that the contents of the remote data base can be electronically transferred to the host data base 25.

The primary operative components of read/write station 15 are illustrated in relation to a sample bottle 37 in FIG. 3. The major operative read/write station components are a print head 39, a reflective sensor 41, a pedestal 43, a pinch roller 45, and two bearings 47 and 49. Pedestal 43 supports bottle 37 from below. Pinch roller 45 presses bottle 37 against the two bearings 47 and 49 for lateral support. Pinch roller 45 then serves to rotate bottle 37 relative to print head 39 and sensor 41 so that a label 51 on bottle 37 can be printed on and read from.

Print head 39 serves to print an identification code. The preferred print head is a thermal ink jet print head used in the wellknown Thinkjet printer; both print head and printer are manufactured by Hewlett-Packard Company as product numbers HP92261 and HP82225B, respectively. These print heads are inexpensive, reliable, and compact.

Currently, such thermal ink jet print heads have sufficient resolution to produce bar code representations of six characters on a standard 2 mL laboratory bottle. However, more than six characters are required or preferred by most analytical laboratories. By using a parallel track bar code, such as that illustrated in FIG. 4, the linear resolution of the print head 39 is effectively multiplied by the number of tracks. The actual gain is somewhat greater since increasing the number of tracks does not require proportionate increases in system codes such as check sum characters. For example, the two-code permits thirteen characters to be encoded on a labelfor a 2 mL bottle. Additional gains are also implemented as described below, eliminating the need for start/stop characters. Thus, the parallel-track bar code format allows the thermal ink jet print head to be employed practically, which in turn makes read/write station 15 and field station 21 practical.

Print head 39 includes 12 nozzles, six of which are dedicated to the upper bar code track and six of which are dedicated to the lower bar code track of the parallel track bar code shown in FIG. 4. Thus the parallel bar code track is printed in a single rotation cycle of bottle 37. A text line is printed on a different cycle. To print text below the bar code, print head 39 is moved downward relative to bottle 37. The reflective sensor 41 pivots as indicated so that the top and bottom bar code tracks can be read separately. The print head 39 and sensor 41 are aligned with respective bearings 47 and 49, which thus serve to maintain optimal spacing between those components and bottle 37.

Pinch roller 45, print head 39, reflective sensor 41, and bearings 47 and 49 retract radially to permit insertion and removal of bottle 37. These components are coupled to engage an inserted bottle in a coordinated fashion so that different size bottles, or other containers with circular symmetry, are accommodated. Proper spacing of the print head 39 and the sensor 41 is maintained since these components are rigidly coupled to respective bearings 47 and 49 which contact the bottle surface. The use of pinch roller 45 to rotate an inserted bottle ensures a constant circumferential print and read speed over different bottle diameters.

As shown in FIG. 3, label 51 does not extend all the way around the circumference of bottle 37. Instead a gap 53 is defined between the label ends. This gap 53 can be used to locate the ends of label 51 so that writing and reading can begin at appropriate positions of label 51. Reflective sensor 41 is angled with respect to the glass surface of bottle 37 so that the specular reflection by the glass is not detected by sensor 41. The diffuse reflection of blank areas of label 51 are detected. Thus, gap 53 appears as a wide black bar to sensor 41.

Gap 53 is selected to have between two and four times the width of the widest bar in the bar code so that it can be distinguished from printing. The bar code itself comprises four characters, thin lines and thin spaces, 6 ink jet dots high by one dot circumferentially, and thick lines and thick spaces, six dots high by three dots circumferentially. The gap is thus selected to be between 6 and 12 dots circumferentially.

The use of a pinch roller to provide a read speed which is independent of bottle circumference and the use of the gap to locate the beginning and end for bar codes eliminates the need for boundary and synchronization codes for bar codes designed for reading by a manually operated wand. These features combine with the parallel-track bar code format to yield encoding of information required by most laboratories, despite the less than lithographic resolution currently available from compact thermal ink jet print heads.

The mechanisms required for implementing the described embodiment, including the required structural members, motors, gears and actuators, are well within the design capabilities of those skilled in the art. However, attention must be paid to obtaining optimal ink jet dot size. If the dots are too small, spaces may be detected between what are supposed to be adjacent dots. Similarly, if the dots are too big, intermediate spaces can be covered with ink. Both of these situations can induce errors.

Optimal control over ink jet drop direction, size and shape is afforded at the point where the droplet breaks away from the nozzles through which it was produced. This is generally about 0.030" from the orifice plate in which the nozzles are formed. Thus, the bearing above the print head should be positioned to maintain a 0.030" to 0.040" spacing between the nozzles and the label.

Another factor in dot size is the paper selected. Paper composition is perhaps the most influential dot integrity parameter. Paper fiber, gauge, density and the presence of certain clay coatings of the fibers influence ink spreading, feathering roundness, penetration, drying speed, color fastness and solvent resistance of the printed dot. Using the illustrated print head, a dot spread factor of 4.2 to 4.5 is desirable to provide equal dimensions of bars and spaces while allowing sufficient overlap of dots to produce continuous vertical bars. Spread factor is a function of both ink rheology and the paper, and therefore must be found empirically. Most of the desired paper properties for bar code are accommodated through certain clay surface coatings which contain surfactants that control ink spread and provide bonding sites for the ink to promote solvent resistance.

Many modifications of the foregoing embodiments are provided by the present invention. With proper programming, the present invention provides for improved human error checking. This is best illustrated by a hypothetical example. Assume that a collector is assigned to collect samples from ABC company and XYZ company. The host computer assigns to the remote station identification numbers starting with ABC001 and XYZ501. (Prior samples were presumably collected regarding XYZ, Inc.) As samples are collected, the remote station can use satellite telemetry data, time or collector responses to structured queries to select identification codes.

For example, the bottle containing a sample from the first assigned site could have encoded thereon bar code and text representations for "001ABC87JUN25". This would communicate to a human reader that the contents were collected on June 25, 1987 and were the first to be collected in a study concerning possible pollution by ABC company. Upon reading by read/write station 15, the sample would be associated automatically with the information under data base identifier ABC001.

The use of such codes would make it much easier for a clerk to ensure that a particular sample was referable to a particular study. It would be difficult for a system based on pre-printed labels to match the flexibility of a computer based identification code assignment scheme in providing codes meaningful to humans.

The present invention provides for printing in human readable characters in conjunction with optical character reader circuitry in an alternative read/write station. More flexible encoding schemes are possible with increased resolution, as these are made possible in cost-effective portable units. Different label materials and different inks are provided for. As these materials change, different sensors can be employed.

As a system, the invention provides for printing of a label prior to affixing the label on a container. This alternative provision can accommodate a wider variety of container shapes. Also, this approach avoids damage to the label in the case a container is dipped into a body of water or other liquid to obtain a sample. In this case, the label printer can still automate the relationship between the label contents and a database.

While the foregoing embodiments were directed to sample tracking for forensic purposes, the invention provides for better tracking of scientific and medical samples as well. The computer system can be programmed in a variety of ways to provide additional levels of error checking and further eliminate operator paper work. The invention is compatible with many different automated analysis systems, and can be used with unautomated analysis systems as well. The information can be printed in a variety of formats, including any number of parallel tracks with bar code, human readable code and other codes. These and other variations and modifications of the described embodiments are provided for by the present invention, the scope of which is limited only by the following claims.

What is claimed is:

1. A system comprising:
   a write station; and
   computer means for receiving, processing, storing and transmitting data and commands, said computer means including:
   data base means for storing descriptive sample data in association with a sample identifier referable to a sample in a sample container,
   access means for sending data to be encoded and written by said write station, and
   processor means, coupled to said data base means and said access means for causing data referable to said sample identifier to be sent via said access means to said write station so that said write station writes a sample identificatiion code referable to said sample identifier on said sample container.

2. The system of claim 1 wherein said write station includes container receiving means for receiving a sample container.

3. The system of claim 1 wherein said write station includes a print head and rotation means for rotating said container relative to said print head as said sample identification code is being written on said container.

4. The system of claim 1 wherein said write station can write said simple identification code in a parallel-track bar code format.

5. The system of claim 1 wherein said write station includes an ink jet head for printing on said sample container.

6. The system of claim 1 wherein said write station includes a thermal ink jet head for printing on said sample container.

7. The system of claim 1 wherein said write station includes read means for reading said sample identification code so that said sample identification code can be verified against said sample identifier and so that said sample can be associated with said descriptive sample data.

8. The system of claim 7 wherein said computer means further includes an operator interface through which said descriptive sample data can be entered and placed in association with said sample identifier in said data base in conjunction with the writing of said identification code on said sample container.

9. The system of claim 7 wherein said write station includes a print head and means for rotating said sample container while said sample identification code is being written on said sample container and while said sample identification is being read from said sample container.

10. The system of claim 9 wherein said read means includes means for detecting ends of a label of said container so that said sample identification code can be written on said label.

11. The system of claim 9 wherein said print head is a thermal ink jet print head capable of printing parallel track bar code data in a single rotational cycle of said sample container.

12. An apparatus comprising:
receiving means for receiving a bottle with a label;
an ink jet print head for printing on said label;
a sensor for reading said label;
rotation means for rotating said bottle relative to said print head and said sensor;
interface means for receiving write and read commands and data to be printed on said label from a host computer and for sending data read from said label to said host computer; and
control circuitry for controlling said print head so that printing referable to data received from said host computer is printed on said label and for controlling said sensor so that print on said label is converted into data to be transmitted to said computer.

13. The apparatus of claim 12 wherein said ink jet head is a thermal ink jet head.

14. The apparatus of claim 13 wherein said control circuitry includes verification circuitry for causing printing to be read after being written so that the data as read can be compared to the data that was to have been printed for verification.

15. The apparatus iof claim 13 wherein said control circuitry causes said print head to print parallel track bar code in a single rotation cycle of said bottle.

* * * * *

UNITED STATES PATENT AND TRADEMARK OFFICE
CERTIFICATE OF CORRECTION

PATENT NO. : 4,855,909

DATED : August 8, 1989

INVENTOR(S) : Kent D. Vincent
Carl A. Myerholtz

It is certified that error appears in the above-identified patent and that said Letters Patent is hereby corrected as shown below:

Column 3, line 31, "is somehoe" should read -- is somehow --

Column 4, line 24, "a labelfor" should read -- a label for --

Column 6, line 67, "said simple identification" should read -- said sample identification --

Column 8, line 26, "apparatus iof claim" should read -- apparatus of claim --

Signed and Sealed this

Twenty-fifth Day of December, 1990

*Attest:*

HARRY F. MANBECK, JR.

*Attesting Officer*    *Commissioner of Patents and Trademarks*